US011166659B2

(12) United States Patent
Urano et al.

(10) Patent No.: US 11,166,659 B2
(45) Date of Patent: Nov. 9, 2021

(54) BLOOD TEST KIT AND BLOOD ANALYSIS METHOD

(71) Applicant: FUJIFILM Corporation, Tokyo (JP)

(72) Inventors: Hikaru Urano, Kanagawa (JP); Shinya Sugimoto, Tokyo (JP); Isao Yonekubo, Tokyo (JP)

(73) Assignee: FUJIFILM Corporation, Tokyo (JP)

( * ) Notice: Subject to any disclaimer, the term of this patent is extended or adjusted under 35 U.S.C. 154(b) by 222 days.

(21) Appl. No.: 16/454,062

(22) Filed: Jun. 27, 2019

(65) Prior Publication Data

US 2019/0313958 A1    Oct. 17, 2019

Related U.S. Application Data

(63) Continuation of application No. PCT/JP2017/047204, filed on Dec. 28, 2017.

(30) Foreign Application Priority Data

Dec. 28, 2016  (JP) .............................. JP2016-255673

(51) Int. Cl.
*B01L 3/00* (2006.01)
*G01N 1/10* (2006.01)
(Continued)

(52) U.S. Cl.
CPC .. *A61B 5/150755* (2013.01); *A61B 5/150351* (2013.01); *G01N 1/10* (2013.01);
(Continued)

(58) Field of Classification Search
CPC ........ A61B 5/150755; A61B 5/150022; A61B 5/150015; A61B 5/150007; A61B 5/15;
(Continued)

(56) References Cited

U.S. PATENT DOCUMENTS 4,477,575 A    10/1984  Vogel et al.
4,910,150 A *   3/1990  Doeding ................ D21H 13/40
                                                           436/69
(Continued)

FOREIGN PATENT DOCUMENTS

CN         1169886       1/1998
CN       101862564      10/2010
(Continued)

OTHER PUBLICATIONS

Office Action of Japan Counterpart Application, with English translation thereof, dated Apr. 7, 2020, pp. 1-6.
(Continued)

*Primary Examiner* — Christine T Mui
(74) *Attorney, Agent, or Firm* — JCIPRNET

(57) ABSTRACT

An object of the present invention is to provide a blood test kit and a blood analysis method, which are for performing quantitative analysis of components by precisely obtaining a dilution factor. According to the present invention, provided is a blood test kit for analyzing a concentration of a target component in a blood sample using a normal component which is homeostatically present in blood, the kit including a diluent solution for diluting the blood sample, a first storing instrument for storing the diluent solution, a separation instrument for separating and recovering blood plasma from the blood sample diluted with the diluent solution, a holding instrument for holding the separation instrument, a second storing instrument for storing the recovered blood plasma, and a sealing instrument for keeping the stored blood plasma within the second storing instrument, in which the separation instrument is composed of glass fiber coated with a resin.

6 Claims, 3 Drawing Sheets

(51) Int. Cl.
- A61B 5/15 (2006.01)
- G01N 1/38 (2006.01)
- G01N 33/49 (2006.01)
- A61B 5/00 (2006.01)

(52) U.S. Cl.
CPC .............. *G01N 1/38* (2013.01); *G01N 33/491* (2013.01); *A61B 5/1405* (2013.01); *A61B 5/150022* (2013.01); *A61B 5/150343* (2013.01); *B01L 2200/0605* (2013.01); *B01L 2300/028* (2013.01); *B01L 2300/042* (2013.01)

(58) Field of Classification Search
CPC ........ A61B 5/150351; A61B 5/150343; A61B 5/1405; A61B 5/14; G01N 1/10; G01N 1/38; G01N 33/491; G01N 33/48; B01L 2200/0605; B01L 2300/028; B01L 2300/042
USPC ......................................................... 422/430
See application file for complete search history.

(56) References Cited

U.S. PATENT DOCUMENTS

| | | | |
|---|---|---|---|
| 5,979,669 | A | 11/1999 | Kitajima et al. |
| 6,170,671 | B1 | 1/2001 | Kitajima et al. |
| 2001/0055784 | A1 | 12/2001 | Noda et al. |
| 2002/0153316 | A1 | 10/2002 | Nanba et al. |
| 2003/0175167 | A1 | 9/2003 | Takanori et al. |
| 2004/0141888 | A1 | 7/2004 | Nanba et al. |
| 2006/0016747 | A1 | 1/2006 | Sakaino et al. |
| 2008/0210644 | A1* | 9/2008 | Milunic ................ D21H 13/40 210/767 |
| 2015/0231536 | A1* | 8/2015 | Nogami ................ B01L 3/502 210/235 |
| 2017/0205433 | A1 | 7/2017 | Osawa et al. |

FOREIGN PATENT DOCUMENTS

| | | |
|---|---|---|
| EP | 0045476 | 2/1982 |
| EP | 1618940 | 1/2006 |
| JP | S5753661 | 3/1982 |
| JP | H02208565 | 8/1990 |
| JP | H04208856 | 7/1992 |
| JP | 2000254461 | 9/2000 |
| JP | 2001221794 | 8/2001 |
| JP | 2001330603 | 11/2001 |
| JP | 2003161729 | 6/2003 |
| JP | 2006038512 | 2/2006 |
| JP | 2009109196 | 5/2009 |
| JP | 2009122082 | 6/2009 |
| JP | 2016118565 | 6/2016 |
| WO | 2012143894 | 10/2012 |
| WO | 2016013388 | 1/2016 |

OTHER PUBLICATIONS

"International Search Report (Form PCT/ISA/210) of PCT/JP2017/047204," dated Apr. 3, 2018, with English translation thereof, pp. 1-5.

"Written Opinion of the International Searching Authority (Form PCT/ISA/237) of PCT/JP2017/047204," dated Apr. 3, 2018, with English translation thereof, pp. 1-10.

Osawa, Susumu, et al., "Delivery Method of the Test Results and the Clinical Laboratory Technology and Offer of the Clinical Laboratory Technology to be Possible at Home," Japanese Journal of Clinical Laboratory Automation, vol. 41, 2016, pp. 154-160.

Osawa, S., et al., "B-257 Development of an assay for measuring biochemical parameters in 65-μL fingertip blood samples collected at home," 68th AACC Annual Scientific Meeting Abstracts, Aug. 2016, p. 1.

"Office Action of China Counterpart Application", dated May 13, 2020, with English translation thereof, p. 1-p. 12.

"Office Action of Europe Counterpart Application", dated Sep. 30, 2020, p. 1-p. 16.

"Search Report of Europe Counterpart Application", dated Nov. 27, 2019, p. 1-p. 9.

"HealthyTokyo—How to take your blood sample for HIV home test kit", Oct. 2, 2016, Available at :"https://www.youtube.com/watch?v=Uph-AOrg7vw".

Jeannette Gootjes et al., "Laboratory evaluation of a novel capillary blood sampling device for measuring eight clinical chemistry parameters and HbA1c", Clinica Chimica Acta, vol. 401, No. 1-2, Mar. 1, 2009, pp. 152-157.

Sugimoto Shinya et al., "Development of an assay of seven biochemical items, HbA1c, and hematocrit using a small amount of blood collected from the fingertip", Clinica Chimica Acta, vol. 413, No. 1-2, Jan. 1, 2012, pp. 192-197.

Masatoshi Horita et al., "Establishment of mail medical examination system using immediate plasma separating device by the self-collection blood—the method of dilution ratio calculation by using Internal standard for the sample with different amount of collecting blood", Rinsho Byori/ Japanese Journal of Clinical Pathology, vol. 56, No. 7, Jul. 25, 2008, pp. 577-583.

"Office Action of China Counterpart Application," with English translation thereof, dated Dec. 11, 2019, p. 1-p. 14.

* cited by examiner

BLOOD TEST KIT AND BLOOD ANALYSIS METHOD

CROSS-REFERENCE TO RELATED APPLICATIONS

This application is a Continuation of PCT International Application No. PCT/JP2017/047204 filed on Dec. 28, 2017, which claims priority under 35 U.S.C § 119(a) to Japanese Patent Application No. 2016-255673 filed on Dec. 28, 2016. Each of the above application(s) is hereby expressly incorporated by reference, in its entirety, into the present application.

BACKGROUND OF THE INVENTION

1. Field of the Invention

The present invention relates to a blood test kit and a blood analysis method, which are for analyzing a target component in a small volume of a blood sample.

2. Description of the Related Art

As blood collection, in general, there are general blood collection in which a qualified person such as a doctor collects blood from the vein using a syringe, and self-blood collection in which a subject to be tested pricks his finger and the like using a blood collection needle so as to collect blood.

The blood collected by the general blood collection is transported to a medical institution or a test institution in a state of being sealed in a blood collection container, and tests are performed therein. In a case where the blood is transported without separating blood cells and blood plasma, tests are performed after a medical institution or a test institution separates the blood into blood cells and blood plasma with a centrifuge. In addition, in the self-blood collection which is performed by a subject to be tested, the collected blood is separated into blood cells and blood plasma by a separation membrane, the blood is transported to a test lab in this separated state, and then tests are performed therein.

JP2003-161729A discloses a method for testing a blood sample collected by self-blood collection. JP2003-161729A specifically discloses a method for quantitatively determining a component to be quantitatively determined in a biological specimen, the method including 1) step of preparing a specimen for quantitation composed of a biological specimen with an unknown volume which contains a component to be quantitatively determined, which is collected without quantitatively determining a volume thereof, and an aqueous solution with a certain volume which contains a certain amount of an indicator substance; 2) step of obtaining a dilution factor (a) of the biological specimen from a concentration ($C_1$) of the indicator substance in the aqueous solution with a certain volume which contains a certain amount of the indicator substance, and a concentration ($C_2$) of the indicator substance in the specimen for quantitation; 3) step of obtaining a concentration (Y) of the component to be quantitatively determined in the specimen for quantitation; and 4) step of determining the component to be quantitatively determined in the biological specimen from the dilution factor (a) of the biological specimen obtained in 2), and the concentration (Y) of the substance to be quantitatively determined in the specimen for quantitation obtained in 3).

JP2001-330603A discloses a quantitative analysis method in which an amount of a target component to be analyzed in a sample is measured; an amount of a normal component other than the target component to be analyzed, which is originally and homeostatically present in the sample, is measured; a volume of the sample is determined from the amount of this normal component and a known concentration of the normal component in the sample; and a concentration of the target component to be analyzed in the sample is determined from the volume of this sample and the amount of the target component to be analyzed.

In addition, JP2009-122082A discloses that, using an instrument for blood dilution and quantitation, a small volume of blood is collected from a human or an animal, and after dilution or without dilution, a certain volume thereof is supplied to another instrument or container or is directly supplied to a reagent. Furthermore, JP2009-109196A discloses a method for quantitatively determining a concentration of a component to be quantitatively determined in a biological specimen by utilizing an absorbance of an indicator substance in an aqueous solution for dilution.

Currently, a method using an indicator substance disclosed in JP2003-161729A, so called an internal standard substance, is adopted in commercially available blood test kits.

Meanwhile, measurement of the type and concentration of components in blood, such as metabolites, proteins, lipids, electrolytes, enzymes, antigens, and antibodies, is generally carried out using blood plasma or blood serum obtained by centrifuging whole blood as a sample. However, centrifugation requires time and effort. A dedicated device is required to carry out centrifugation, and the centrifugation takes at least 10 minutes or longer. Therefore, in place of the centrifugation, a method for separating whole blood into blood plasma by filtration has been examined. Regarding this filtration method, JP1990-208565A (JP-H02-208565A) and JP1992-208856A (JP-H04-208856A) disclose several methods in which a column is filled with a glass fiber filter paper, whole blood is injected from one side of the column, pressurization and depressurization are performed, and blood plasma is obtained from the other side thereof. In addition, JP1982-053661A (JP-S57-053661A) and JP2000-254461A disclose blood filtration with glass fibers.

SUMMARY OF THE INVENTION

In the method disclosed in JP2003-161729A, it is required that a ratio of a diluent solution to a blood sample volume be set high in a case of a small volume of a blood sample. However, in this case, a change rate in a volume of a diluent solution before and after diluting the blood sample becomes very small, and thus a change rate in a concentration of an internal standard substance becomes small. Therefore, there is a problem of a decrease in level of repeatability and reproducibility with respect to measurement values.

JP2001-330603A discloses that about 100 µL of whole blood of a healthy subject is added dropwise to a porous membrane, blood cells are separated to develop blood serum, and thereafter, a solution obtained by adding 150 µL of a physiologically isotonic phosphate-buffered saline (PBS, pH of 7.4) thereto is centrifuged, and a supernatant thus obtained is analyzed as an analytical specimen, but does not disclose collection of blood of less than 100 µL.

In the method of JP2009-122082A, 10 µL of a blood volume is precisely collected with a micropipette so as to be analyzed, but in a case where the blood is collected by a patient who lacks experience in blood collection, it is difficult to precisely collect a certain volume thereof, resulting in errors in measurement values in a case where tests are performed with collected blood volumes including errors.

The measurement method disclosed in JP2009-109196A is the measurement with a dilution factor of about 10, but in a case where a dilution factor is further raised to sufficiently secure a volume of diluted blood, there is the same problem as in JP2003-161729A of a decrease in level of repeatability and reproducibility with respect to measurement values.

As described above, a blood analysis method in which a level of repeatability and reproducibility with respect to measurement values is high in a case of using a small volume of a blood sample, is desired. The inventors of the present invention have examined a method in which an external standard substance is used in consideration that using an internal standard substance, which has been proposed in the related art, is not sufficient for performing analysis with high accuracies.

In addition, using the glass fibers disclosed in JP1990-208565A (JP-H02-208565A), JP1992-208856A (JP-H04-208856A), and JP1982-053661A (JP-S57-053661A) to perform blood filtration is a method capable of suppressing a pressure increase at the time of blood filtration, thereby easily performing separation without destroying blood cells. However, there is disadvantage of components such as sodium and chloride contained in the glass fiber being eluted into a diluent solution and thereby affecting measurement. In order to solve this problem, in JP2000-254461A, a carbon thin film is formed on a surface of the glass fiber by vapor deposition under vacuum to suppress an amount of sodium elution. However, there is a problem of cost and time consuming in manufacture of glass fibers by vacuum vapor deposition.

An object of the present invention is to provide a blood test kit and a blood analysis method, which are for quantitatively analyzing a component by precisely obtaining a dilution factor, at accuracy not described in the related arts of, for example, JP2003-161729A and JP2001-330603A by enabling a reduction in concentration of normal components eluted from members of the blood test kit to a level that has substantively no influence in a method for analyzing a concentration of a target component in a blood sample by using a normal component homeostatically present in blood as a method for quantitatively analyzing a component by diluting a small volume of blood with a buffer solution. Another object of the present invention is to provide a blood test kit and a blood analysis method, which are capable of further improving accuracies by using a method for obtaining a dilution factor using an internal standard in combination.

As a result of intensive studies to achieve the above-described objects, the inventors of the present invention have found that the above-described objects can be achieved by using a separation instrument which is composed of glass fiber coated with a resin in a blood test kit including a diluent solution for diluting the blood sample, a first storing instrument for storing the diluent solution, a separation instrument for separating and recovering blood plasma from the blood sample diluted with the diluent solution, a holding instrument for holding the separation instrument, a second storing instrument for storing the recovered blood plasma, and a sealing instrument for keeping the stored blood plasma within the second storing instrument; and therefore have completed the present invention. That is, according to the present invention, the following inventions are provided.

(1) A blood test kit for analyzing a concentration of a target component in a blood sample using a normal component which is homeostatically present in blood, the kit comprising:
a diluent solution for diluting the blood sample;
a first storing instrument for storing the diluent solution;
a separation instrument for separating and recovering blood plasma from the blood sample diluted with the diluent solution;
a holding instrument for holding the separation instrument;
a second storing instrument for storing the recovered blood plasma; and
a sealing instrument for keeping the stored blood plasma within the second storing instrument,
in which the separation instrument is composed of glass fiber coated with a resin.

(2) The blood test kit according to (1), in which the resin is a resin selected from the group consisting of acrylic resins, urethane resins, polyvinyl alcohol resins, and epoxy resins.

(3) The blood test kit according to (1) or (2), in which a coating amount of the resin is 1% to 10% by mass with respect to a mass of the glass fiber.

(4) The blood test kit according to any one of (1) to (3), in which a volume of the diluent solution is four or more times a volume of the blood plasma.

(5) The blood test kit according to any one of (1) to (4), in which the normal component which is homeostatically present in blood is sodium ions or chloride ions.

(6) The blood test kit according to any one of (1) to (5), in which the normal component which is homeostatically present in blood is sodium ions or chloride ions, and another normal component which is homeostatically present in blood.

(7) The blood test kit according to (6), in which the other normal component is total protein or albumins.

(8) A blood analysis method, comprising:
a step of diluting a collected blood sample with a diluent solution using the blood test kit according to any one of (1) to (7);
a step of determining a dilution factor by using a normal value of a normal component which is homeostatically present in blood; and
a step of analyzing a concentration of a target component in the blood sample.

According to a blood test kit and a blood analysis method of the present invention, a concentration of a target component in a blood sample can be analyzed with high accuracies using a normal component which is homeostatically present in blood.

DESCRIPTION OF THE PREFERRED EMBODIMENTS

Figure 1:
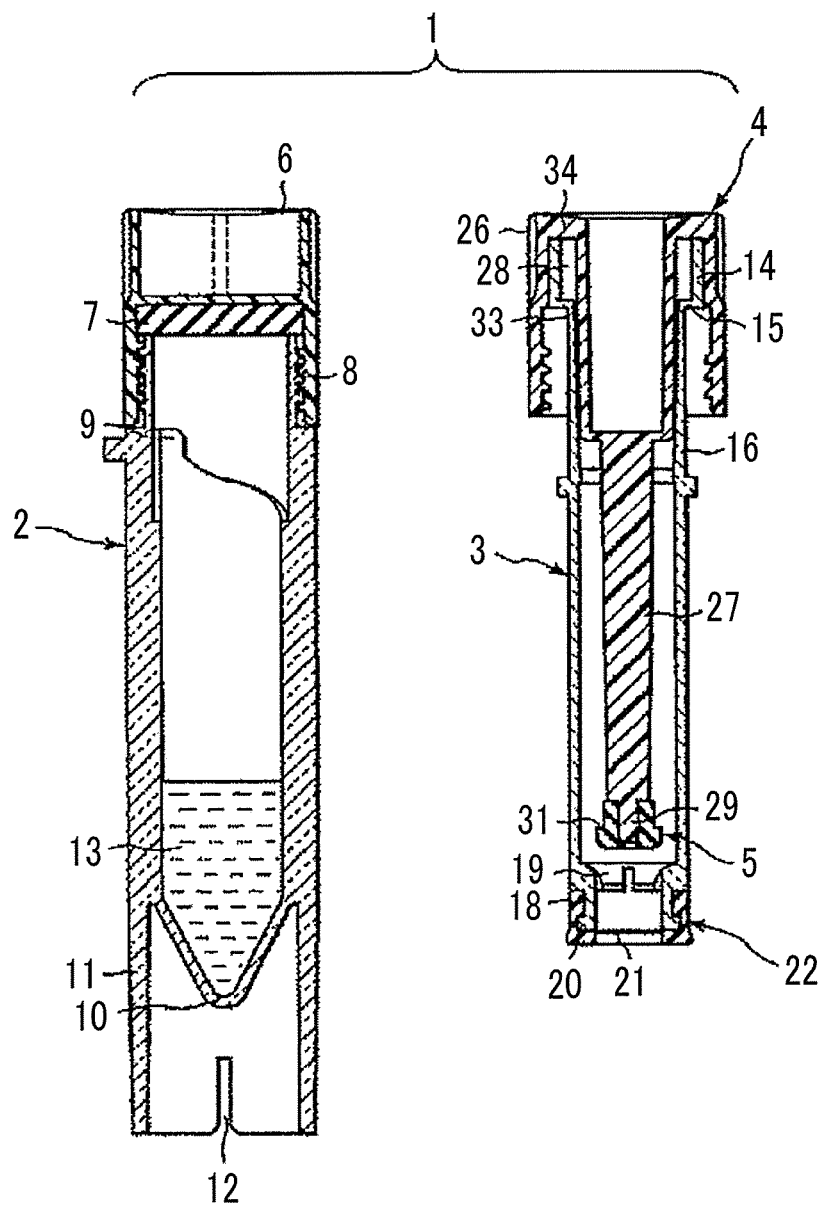
FIG. 1 is a cross sectional diagram of a blood test kit according to an embodiment of the present invention.

Hereinafter, an embodiment of the present invention will be described. A range indicated by X to Y includes values of an upper limit X and a lower limit Y. A normal component which is homeostatically present in blood may be referred to as an external standard substance or an external standard. In addition, a normal component which is not present in blood may be referred to as an internal standard substance or an internal standard.

As a method of collecting a small volume of blood, a method of performing blood analysis using a filter paper is disclosed in JP1998-104226A (JP-H10-104226A). Furthermore, a method of using a porous material having a high level of blood retention property instead of a filter paper is disclosed in JP2001-330603A. In these methods, because blood components absorbed into a material is extracted with a buffer solution and the like so as to be measured, sodium ions, chloride ions, calcium ions, proteins, and the like which are external standard substances homeostatically present in blood are used reference substances for estimating a dilution factor by a buffer solution in a case where blood is eluted and redissolved. In these methods, in a case where a volume of blood collection varies and a dilution factor of the collected blood becomes large, the accuracy of analysis thereafter decreases, and thus results vary. Because the blood is once coagulated and solidified, the stability of the target component to be analyzed is not sufficiently secured in some cases. Furthermore, as a buffer solution for extracting a biological component from a dried specimen, it is necessary to use a buffer solution into which NaOH, NaCl, or HCl is added in order to adjust pH and stabilize the biological component. For this reason, there was a problem in which concentrations of sodium ions and chloride ions which are homeostatically present at a relatively high concentration among components of a specimen and which have little difference between individuals, cannot be used as external standards for correcting a concentration of another original biological component of the diluted specimen.

Meanwhile, the method is disclosed in JP2003-161729A as a method for diluting a small volume of collected blood with a buffer solution into which an internal standard is added, and quantitatively determining components present in diluted blood plasma at an unknown amount from a dilution factor of an internal standard substance. N-(2-hydroxy-3-sulfopropyl)-3,5-dimethoxyaniline sodium salt (HSDA) or acid blue 9 (brilliant blue FCF) is used as an internal standard substance, and a buffering agent and a preservative are used for stably maintaining blood. Such a formulation has realized maintaining of stability of components thereof by not coagulating blood, but in a case where volumes of blood collected vary and a collected volume is small, there still were problems in which a dilution factor of an internal standard substance after dilution becomes small, and reliability of test accuracies deteriorates because an amount of blood components itself decreased. In addition, in the method of dilution with a buffer solution, a biological component is stored in a buffer solution at a physiological condition of pH 7.4, and is excellent in stability during transportation, but because a dilution factor of an internal standard, which is obtained by adding a specimen into a buffer solution into which the internal standard is added, is small and there is a problem in which measurement errors are likely to occur in a case where only a small amount of a specimen is added.

In addition, in examples of these related arts, a phosphate buffered saline is used in a buffer solution for extraction because the phosphate buffered saline is excellent for stably maintaining a biological component, but the phosphate buffered saline contains sodium ions or chloride ions. For this reason, sodium ions and chloride ions cannot be used external standards, and thus calcium ions, proteins, and the like are used. Accordingly, for performing a blood test using a small volume of blood with high accuracies, use of an external standard substance for correcting a dilution factor as disclosed in the related art and use of a buffer solution containing an internal standard substance proposed in the related art were not sufficient for ensuring test accuracies.

In addition, even in a case of homeostatic substances in blood, in sodium ions for example, a distribution width of a normal value is 134 to 146 mmol/L, and therefore it is necessary to more precisely calculate a dilution factor. A decrease in accuracies of a dilution factor affects a bad influence on test accuracies, thereby making a risk of a deterioration in reliability of a test high. Particularly, in a case where even little contamination due to an external standard substance eluted from a member constituting a kit into a buffer solution is present, and in a case where a volume of blood collected is large or small, a degree of influence of the contamination on calculation of a dilution factor varies. JP2001-330603A does not all mention about maintaining, constant, such a degree of influence of the contamination due to the external standard substance eluted from the member constituting the kit into the buffer solution, on the calculation of the dilution factor.

In addition, JP2003-161729A discloses about an internal standard, but does not disclose use of an external standard in combination. Accordingly, there is no disclosure regarding the contamination due to the external standard, and specific means for preventing the contamination has not been proposed at all.

An object of the present invention is to provide a blood test kit for analyzing a concentration of a target component by diluting a small volume of a blood sample with a buffer solution, the method capable of obtaining a dilution factor with accuracies not described in the related art in a case where analysis of a control component is performed using an external standard homeostatically present in blood. A solution for achieving the above-described object is the blood test kit that reduces a concentration of normal components eluted from members of the blood test kit to a level that has substantively no influence. Specifically, a separation instrument is a separation instrument composed of glass fiber coated with a resin. In addition, in a preferred embodiment, not only an external standard but also an internal standard is used.

According to the present invention, in the measurement method for measuring a target component to be analyzed in blood, it is possible to minimize homeostatic normal components eluted from members constituting the kit by using glass fibers coated with a resin as a blood plasma separation member when a patient himself separates blood into blood plasma after dilution of the blood. Accordingly, it is possible to realize a blood test kit and a blood analysis method, which are capable of accurately quantitatively determining a target component to be analyzed by detecting a homeostatic normal component derived from blood with sufficiently high accuracies. In addition, a blood test kit and a blood analysis method, which are capable of further improving the accuracy by using a method for obtaining a dilution factor with an internal standard in combination are provided.

[1] Blood Test Kit and Blood Analysis Method

A blood test kit of the present invention, which is for analyzing a concentration of a target component in a blood sample using a normal component which is homeostatically present in blood is a blood test kit which includes a diluent solution for diluting the blood sample;

a first storing instrument for storing the diluent solution;

a separation instrument for separating and recovering blood plasma from the blood sample diluted with the diluent solution;

a holding instrument for holding the separation instrument;

a second storing instrument for storing the recovered blood plasma; and a sealing instrument for keeping the stored blood plasma within the second storing instrument, in which the separation instrument is composed of glass fiber coated with a resin.

Analyzing a concentration of the target component in the blood sample includes determining a concentration of the target component (that is, quantitatively determining the target component), determining whether a concentration of the target component is equal to or higher than a predetermined reference value or is equal to or lower than a predetermined reference value, and the like. An aspect of the analysis is not particularly limited.

[Blood Collection Method and Volume Thereof]

The blood test kit of the present invention is used for collecting a blood sample. The collection of blood by the blood test kit of the present invention may be performed by a subject to be tested or by a qualified person such as a doctor.

In a preferred embodiment, a patient himself injures a fingertip and the like using a blade-attached instrument such as a lancet and then collects the blood flowing out of the skin. It is preferable that the blood be collected in a manner of decreased invasiveness so as to alleviate the burden on a patient. It is more preferable to be able to collect the blood painlessly or with extremely little pain when collecting the blood, and in this case, it is desired that a depth and a size of the wound be small, and a volume of blood that can be collected becomes very small. Accordingly, a volume of a sample collected by the blood test kit of the embodiment of the present invention (that is, a volume of blood collected) is preferably 100 µL or less. In the present invention, even with such a small volume of blood collection of a patient, it is possible to suppress a concentration of the normal component which is homeostatically present in blood and may be eluted from the member of the blood test kit into the diluent solution to a level that has substantively no influence, and to provide a method for measuring a component to be analyzed at high measurement accuracy by using, for example, sodium ions or chloride ions as a normal component homeostatically present in blood.

[Normal Component Homeostatically Present in Blood]

As described above, regarding a target component after dilution of diluted blood plasma of which a dilution factor of blood plasma components is large, in order to precisely analyze a concentration of a target component present in blood plasma of blood before dilution, a change rate in concentration becomes extremely small, leading to adverse effects in which measurement errors become high or reproducibility of measurement deteriorates in a method for obtaining a concentration of target component from a change rate in concentration of a substance present in the diluent solution in advance. Accordingly, the blood test kit of the present invention is the blood test kit for analyzing a concentration of a target component in a blood sample by using a normal component which is homeostatically present in blood.

"Use" of a normal component means determination of a dilution factor for analyzing a concentration of a target component based on a homeostatic value (normal value) of the normal component. Accordingly, analyzing a concentration of a target component in a blood sample using a normal component homeostatically present in blood also means that analyzing of a concentration of a target component by determining a dilution factor based on a homeostatic value (a normal value) of the normal component homeostatically present in blood.

Examples of normal components homeostatically present in blood include sodium ions, chloride ions, potassium ions, magnesium ions, calcium ions, total proteins, albumins, and the like. As a concentration of these normal components contained in blood serum and blood plasma of a blood sample, a concentration of sodium ions is 134 to 146 mmol/L (average value: 142 mmol/L), a concentration of chloride ions is 97 to 107 mmol/L (average value: 102 mmol/L), a concentration of potassium ions is 3.2 to 4.8 mmol/L (average value: 4.0 mmol/L), a concentration of magnesium ions is 0.75 to 1.0 mmol/L (average value: 0.9 mmol/L), a concentration of calcium ions is 4.2 to 5.1 mmol/L (average value: 4.65 mmol/L), a concentration of total proteins is 6.7 to 8.3 g/100 mL (average value: 7.5 g/100 mL), and a concentration of albumins is 4.1 to 5.1 g/100 mL (average value: 4.6 g/100 mL). The present invention is for enabling measurement of a target component in a case where a volume of blood to be collected is extremely small for alleviating patient's pain. In a case where a small volume of blood is diluted with a diluent solution, it is required that a concentration of "the normal component homeostatically present in blood," which is present in the diluent solution is accurately measured. As a dilution factor becomes large, a concentration of a component, which is originally present in the blood, in the diluent solution decreases, and depending on dilution factors, measurement errors may be included at the time of measurement of the concentration. Accordingly, it is preferable to measure a normal component present at a high concentration in a small volume of the blood in order to detect the normal component with sufficiently high accuracies when a small volume of blood components is diluted by a large dilution factor. In the present invention, it is preferable to use sodium ions ($Na^+$) or chloride ions ($Cl^-$) which are present at a high concentration among the components homeostatically present in a blood sample. Furthermore, it is most preferable to measure sodium ions which are present in the blood at the largest amount among the above-mentioned normal components homeostatically present in blood. Regarding sodium ions, an average value represents a normal value (a median value within a reference range), and this value is 142 mmol/L accounting for 90 mole % or more of total cations in blood plasma. In the present invention, a normal component which is homeostatically present in blood is preferably sodium ions or chloride ions, or another normal component which is homeostatically present in blood. In this case, the other normal component is preferably total proteins or albumins.

An occupancy rate of blood plasma components in the blood of a subject to be tested is about 55% in terms of a volume ratio, but varies depending on changes in salt intake and the like of the subject to be tested. Therefore, in a case of using the blood test kit of the embodiment of the present invention, a dilution factor of blood plasma is determined by using a normal value of the normal component which is homeostatically present in blood plasma, and a concentration of a target component in blood plasma in a blood sample is analyzed by using the determined dilution factor. As a method for determining a dilution factor, it is possible to obtain a dilution factor by calculating a dilution factor (Y/X)

of the blood plasma components in a blood sample from a measurement value (concentration X) of an external standard substance (for example, sodium ions and the like) in a diluent solution of the blood plasma, and a known concentration value (concentration Y; in a case of sodium ions, 142 mmol/L) of the external standard substance (for example, sodium ions and the like) contained in blood plasma of the blood sample. Using this dilution factor, a measurement value (concentration Z) of a target component in a diluent solution of the blood plasma is measured, and by multiplying this measurement value by the dilution factor, it is possible to measure a concentration [Z×(Y/X)] of a target component to be analyzed actually contained in the blood plasma of the blood sample.

A concentration of sodium ions and a concentration of chloride ions can be measured by, for example, a flame photometric method, a glass-electrode method, a titration method, an ion selective electrode method, an enzyme activity method, and the like.

In a case of measuring sodium ions, it is possible to use an enzymatic assay by which sodium ions in several μL of a specimen of very low sodium concentration (24 mmol/L or less) diluted with a buffer solution are measured by utilizing that the enzyme activity of the enzyme galactosidase is activated by sodium ions. This method can be applied to a biochemical/automated immunoassay analyzer, and is highly efficient and economical for not requiring another measuring instrument for measurement of sodium ions.

In addition, in order to confirm whether the blood test kit in which an amount of a normal component derived from members is defined is actually used, or whether a method for diluting blood and recovering blood plasma is normally performed, it is preferable that an additional dilution factor be separately obtained from another normal component in blood plasma so as to check whether a value thereof matches with the dilution factor obtained above. The term "match" means, with respect to two measurement values (a, b), a ratio of a difference thereof to an average value thereof; that is, (a−b)/{(a+b)/2}×100 is 20% or smaller, is preferably 10% or smaller, and is more preferably 5% or smaller. Accordingly, it is possible to verify that analysis of a concentration of a target component in a blood sample has been normally performed. Examples of normal components homeostatically present in blood plasma, which are other than sodium ions and chloride ions, are preferably selected from total proteins or albumins, and are more preferably total proteins. Examples of methods for measuring total proteins include known methods such as a biuret method, an ultraviolet absorption method, a Bradford method, a Lowry method, a bicinchoninic acid (BCA) method, and a fluorescence method. It is possible to appropriately select a method to be used depending on characteristics, sensitivity, a specimen amount, and the like of a measurement specimen.

[Normal Component not Present in Blood]

As a preferred embodiment, the blood test kit of the embodiment of the present invention is capable of analyzing a concentration of a target component in a blood sample by using a normal component not present in blood together with a normal component homeostatically present in blood.

It is possible to use the normal component not present in the blood by adding the normal component not present in the blood into a diluent solution (to be described later) of a kit such that a concentration thereof becomes a predetermined concentration. As the normal component not present in the blood, it is possible to use a substance which is not contained in the blood sample at all, or is contained therein in an ultra-small amount. As the normal component not present in blood, it is preferable to use substances which do not interfere with the measurement of the target component in the blood sample, substances which do not decompose under the action of biological enzymes in the blood sample, substances which are stable during dilution, substances which do not pass through a blood cell membrane and not contained in the blood cells, substances which are not adsorbed to a storing container of the buffer solution, and substances which can be utilized by a detection system capable of measurement at high accuracy.

As the normal component not present in the blood, substances which are stable even in a case where the substances are stored for a long period of time in a state of being added into the diluent solution, are preferable. Examples of normal components not present in blood include glycerol 3-phosphate, Li, Rb, Cs, or Fr as alkali metal, and Sr, Ba, or Ra as alkaline earth metal. Among these, Li and glycerol 3-phosphate are preferable.

These normal components not present in blood develops color by adding, thereinto, a second reagent at the time of measuring a concentration after blood dilution, and the concentration in the diluted blood can be obtained from a color optical density. For example, regarding measurement of lithium ions added into a diluent solution, a large number of specimens can be easily measured with a small amount of blood by using a chelate colorimetric method (a halogenated porphyrin chelating method: perfluoro-5,10,15,20-tetraphenyl-21H,23H-porphyrin) with an automatic biochemistry analyzer.

By using a blood test kit for analyzing a concentration of a target component in a blood sample using a normal component not present in blood together with a normal component homeostatically present in blood, that is, using two normal components in combination, it is possible to realize analysis having higher reliability.

In the embodiment in which two normal components are used in combination, in a case where sodium ions are used as a normal component homeostatically present in blood and lithium ions are used as a normal component not present in blood, and measurement of sodium ions is carried out by the enzyme activity method utilizing that β-galactosidase activity is in a proportional relationship, and measurement of lithium ions is carried out by the above-described chelate colorimetric method, a dilution factor of a blood sample can be calculated by any one of Formulas 1 to 4.

$$X=(A+C)/(B+D) \quad \text{Formula 1:}$$

$$X=\{(A^2+C^2)^{1/2}\}/\{(B^2+D^2)^{1/2}\} \quad \text{Formula 2:}$$

$$X=a\times(B+D)\times b \quad \text{Formula 3:}$$

(where a and b are coefficients, and a standard curve represented by Formula 3 is prepared in advance by acquiring data of (B+D) and a dilution factor in advance)

$$X=A/B' \quad \text{Formula 4:}$$

(where B'=(A×D)/C)

In the above formulas, A, B, C, D, B', and X are defined as follows.

A: An absorbance in a case of color development of a buffer solution

B: An amount of change in absorbance after adding blood plasma

C: An absorbance at a median value of 142 mmol/L of blood plasma sodium

D: An absorbance at a concentration of sodium ions after diluting blood plasma

B': A correction value of an absorbance of a normal component not present in blood of diluted blood plasma obtained, by a dilution factor calculated from the absorbance of the blood plasma sodium X: A dilution factor of blood plasma As another calculation method for a case of obtaining a dilution factor, an aspect in which a dilution factor is calculated by Formula 5 using a root-mean-square method, a concentration of a target component to be analyzed in a diluent solution is multiplied by the dilution factor calculated by Formula 5, and a concentration of a target component of components in a blood sample is analyzed, is preferable.

$$X=[\{(A/B)^2+(C/D)^2\}/2]^{1/2} \quad \text{Formula 5:}$$

A concentration of a target component of components in a blood sample can be calculated from a concentration of a target component in a diluent solution, based on the above-mentioned dilution factor.

[Diluent Solution]

The blood test kit of the embodiment of the present invention includes the diluent solution for diluting a collected blood sample. The diluent solution for diluting a blood sample is preferably a diluent solution which does not contain a normal component homeostatically present in blood, which is used for obtaining a dilution factor. The phrase "does not contain" in the present specification means that a diluent solution "substantially does not contain" a normal component. The phrase "substantially does not contain" means that a diluent solution does not contain a homeostatic substance used for obtaining a dilution factor at all, or means a case in which, even in a case where a diluent solution contains a homeostatic substance, an ultra-small amount of concentration is contained to the extent that does not affect measurement of a homeostatic substance in a diluent solution after diluting a blood sample. In a case where sodium ions or chloride ions are used as a normal component homeostatically present in blood, a diluent solution which substantially does not contain sodium ions or chloride ions is used as a diluent solution.

In the present invention, after a blood sample collected by a patient or subject to be tested is diluted, it is possible to transport the sample to a medical institution or a test institution so that a concentration of a target component is analyzed. There is a possibility that a long period of time is taken from blood collection to analysis, and therefore during this time, it is preferable to prevent decomposition or denaturation of a target component in a diluent solution of the blood. A pH of blood is generally maintained constant at a pH of about 7.30 to 7.40 for healthy subjects. Accordingly, in order to prevent decomposition or denaturation of a target component, a diluent solution is preferably a buffer solution having a buffering action within a pH range of pH 6.5 to pH 8.0, preferably pH 7.0 to pH 7.5, and further preferably pH 7.3 to pH 7.4, and the diluent solution is preferably a buffer solution containing a buffering component for suppressing variation in pH.

As the type of the buffer solution, there are an acetate buffer solution (Na), a phosphate buffer solution (Na), a citrate buffer solution (Na), a borate buffer solution (Na), a tartrate buffer solution (Na), a Tris (tris(hydroxymethyl) aminoethane) buffer solution (Cl), a HEPES ([2-[4-(2-hydroxyethyl)-1-piperazinyl]ethanesulfonic acid]) buffer solution, a phosphate buffered saline (Na), and the like. Among these, as a buffer solution around pH 7.0 to pH 8.0, a phosphate buffer solution, a Tris buffer solution, and a HEPES buffer solution are representative. However, the phosphate buffer solution contains a sodium salt of phosphoric acid; the Tris buffer solution has a dissociation pKa of 8.08, and thus is usually used in combination with hydrochloric acid for imparting buffering ability around pH 7.0 to pH 8.0; and a dissociation pKa of sulfonic acid of HEPES is 7.55, but in order to prepare buffer solution at constant ionic strength, a HEPES mixture of sodium oxide and sodium chloride is used. From these viewpoints, these solutions are useful as a buffer solution having an action of maintaining pH constant, but contain sodium ions or chloride ions which are substances preferably used as an external standard substance in the present invention, and thus, application thereof to the present invention is not preferable.

As the diluent solution included in the kit of the present invention, it is preferable to use a buffer solution which does not contain sodium ions or chloride ions. The diluent solution used in the present invention is preferably a diluent solution including at least an amino alcohol compound selected from the group consisting of 2-amino-2-methyl-1-propanol (AMP), 2-ethylaminoethanol, N-methyl-D-glucamine, diethanolamine, and triethanolamine, and a buffering agent selected from the group consisting of 2-[4-(2-hydroxyethyl)-1-piperazinyl]ethanesulfonic acid (pKa= 7.55) also called HEPES which is a buffering agent having a pKa around 7.4, N-tris(hydroxymethyl)methyl-2-aminoethanesulfonic acid also called TES (pKa=7.50), 3-morpholinopropanesulfonic acid also called MOPS (pKa=7.20), and N,N-bis(2-hydroxyethyl)-2-aminoethanesulfonic acid also called BES (pKa=7.15), which are Good's buffer solutions (Good's buffers). Among these, a combination of 2-amino-2-methyl-1-propanol (AMP) with HEPES, TES, MOPS, or BES is preferable, and a combination of 2-amino-2-methyl-1-propanol (AMP) with HEPES is most preferable.

For preparing the buffer solution described above, an amino alcohol may be mixed with the Good's buffer solutions at a concentration ratio of 1:2 to 2:1, preferably 1:1.5 to 1.5:1, and more preferably 1:1. A concentration of the buffer solution is not limited, but a concentration of the amino alcohol or the Good's buffer solution is 0.1 to 1000 mmol/L, preferably 1 to 500 mmol/L, and more preferably 10 to 100 mmol/L.

A chelating agent, a surfactant, an antibacterial agent, a preservative, a coenzyme, a saccharide, and the like may be contained in the buffer solution in order to keep a target component to be analyzed stable. Examples of chelating agents include a salt of ethylenediaminetetraacetic acid (EDTA), citrate, oxalate, and the like. Examples of the surfactant include a cationic surfactant, an anionic surfactant, an amphoteric surfactant, and a nonionic surfactant. Examples of the preservative include sodium azide, antibiotics, and the like. Examples of the coenzyme include pyridoxal phosphate, magnesium, zinc, and the like. Examples of the saccharide of a red blood cell-stabilizing agent include mannitol, dextrose, oligosaccharide, and the like. Particularly, by adding the antibiotics, it is possible to suppress the growth of bacteria which are partially mixed from the surface of the finger at the time of collecting blood from the finger, and stabilize the decomposition of biological components by bacteria.

It is important that these buffer solutions do not contain a normal component homeostatically present in blood and an internal standard substance, and do not interfere with a measuring system. In addition, it is preferable that components diluted with these buffer solutions are not interfered even by various measuring methods using the biochemical/automated immunoassay analyzer, that blood cells are not hemolyzed, and that biological components can be stored stably even at 37° C.

In a case where whole blood is used for a blood sample, blood cell components in diluted blood is required to be separated through a filter, and by setting osmotic pressure of the buffer solution equivalent to (285 mOsm/kg (mOsm/kg is an osmotic pressure that 1 kg of water of the solution has, and indicates millimoles of ions)) or higher than that of the blood, it is possible to prevent hemolysis of blood cells. The osmotic pressure can be adjusted to be isotonic by measurement of a target component; salts, sugars, or buffering agents, which do not affect measurement of a normal component homeostatically present in blood; and the like.

As a measurement method in which blood plasma sodium ions diluted with a buffer solution is used as a normal component homeostatically present in blood, there are the flame photometry, the atomic absorption method, and the ion selective electrode method. In the present invention, a specimen obtained by collecting a small volume of blood from the finger and diluting the blood with a buffer solution is only about 150 μL, and it is preferable that measurement of a normal component homeostatically present in blood can be performed with a small volume of several μL because 10 or more items of biochemical components and immunological test items are measured. In addition, since it is necessary to analyze a large number of specimens, it is preferable that application thereof to a commercially available biochemical/automated immunoassay analyzer is possible.

[Volume of Diluent Solution and Dilution Factor]

In a case of testing a specific organ or a specific disease such as liver function, renal function, metabolism, and the like as a blood test, analysis of a plurality of target components to be measured is generally performed at the same time in order to perform a prediction and the like of a state of the organ, a lifestyle habit, and the like by obtaining information of the plurality of target components to be measured which are specific to the organ or the disease. For example, in order to test the state of a liver, generally, a concentration of various types of substances in the blood such as ALT (alanine transaminase), AST (aspartate aminotransferase), γ-GTP (γ-glutamyl transpeptidase), ALP (alkaline phosphatase), total bilirubin, total protein, and albumins is measured. As above, in order to measure the plurality of target components from one blood sample, a certain volume of diluted blood is required in a case of considering a possibility of measuring again. Accordingly, regarding a diluent solution for diluting the collected blood, it is important that a certain volume thereof is secured. A volume of the diluent solution in the kit is preferably 4 times or more a volume of blood plasma (that is, a dilution factor is 5 times or more a volume of blood plasma), is more preferably 10 times or more, and is even more preferably 14 times or more. For example, in a case where a volume of blood collected is 50 μL, and in a case where a rate of an amount of blood plasma in the volume of blood collected is 0.55, a volume of blood plasma can be calculated as 27.5 μL, and in a case where the diluent solution is 360 μL, a dilution factor is 14. Assuming a volume of blood plasma and a volume of diluent solution, which are obtained by calculation from a dilution factor in a case of using blood plasma as a reference, are R and S, respectively, a dilution factor can be estimated with the blood sample as a reference by obtaining (R+0.55×S)/R. A volume of diluent solution used for the blood analysis is preferably 2.7 times or more, more preferably 6.0 times or more, and even more preferably 8.2 times or more with respect to a volume of a blood sample.

[Separation Instrument for Separating and Recovering Blood Plasma from Dilution of Blood Sample]

There is a possibility that a blood sample collected by the blood test kit of the embodiment of the present invention is left alone for a long period of time in a diluted state before performing the analysis. During the time, for example, in a case where red blood cells are hemolyzed, substances, enzymes, and the like which are present in the blood cells are eluted into the blood plasma or blood serum, and therefore a test result is affected thereby. Furthermore, there is a possibility that an absorption amount of the eluted hemoglobin affects a case of measuring an amount of a target component to be analyzed with light information such as the optical absorption of the target component to be analyzed, and the like. Therefore, it is preferable that the hemolysis is prevented. For this reason, an aspect in which a separation instrument for separating and recovering blood plasma from a dilution of a blood sample is contained in a blood test kit is preferable. A preferred example of the separation instrument is a separation membrane. It is possible to use the separation membrane such that blood cells are separated and blood plasma components are recovered by applying pressure to the diluent solution of a blood sample, trapping the blood cell components with the separation membrane, and allowing the blood plasma components to pass through the separation membrane. The separation membrane is preferably glass fibers, and in the present invention, glass fibers are used. Before and after blood separation, it is preferable to use an anticoagulant. In addition, in order to ensure the accuracy of measurement, it is preferable that backflow of the blood plasma passed through the separation membrane to the blood cells side does not occur. Therefore, specifically, the kit can include a backflow prevention means described in JP2003-270239A as a constituent component.

[Glass Fiber Coated with Resin]

Figure 3:
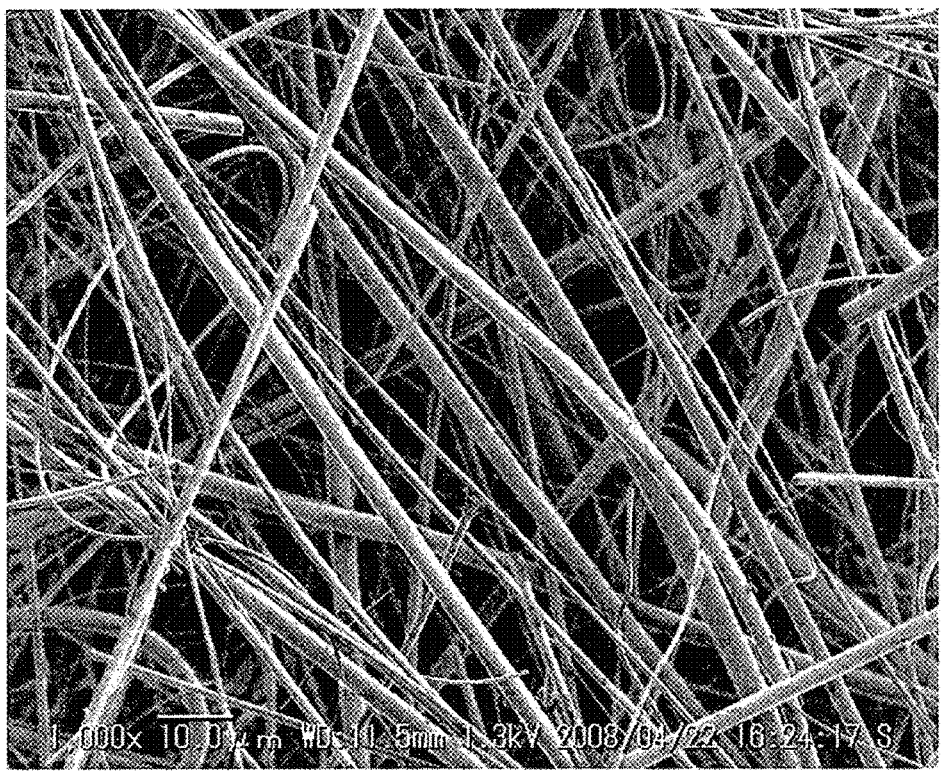
FIG. 3 is a scanning electron microscope (SEM) photograph of glass fibers not coated with a resin.
Figure 4:
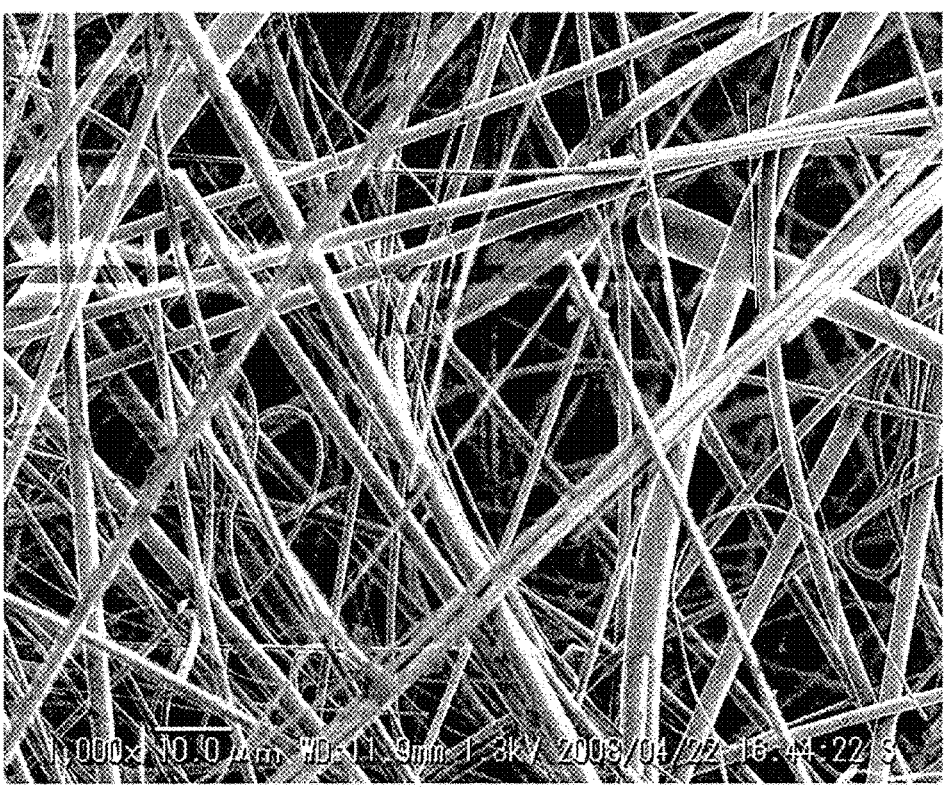
FIG. 4 is a SEM photograph of glass fibers coated with a resin.

In the blood test kit of the embodiment of the present invention, it is required to suppress an amount of a normal component homeostatically present in blood, which is derived from the members of the blood kit and may be contained diluted blood plasma, to a level that has substantively no influence. A representative normal component homeostatically present in blood is sodium ions, but the glass fiber that is the member of the separation instrument contains sodium ions as a component. Therefore, in a case of detecting a concentration of sodium ions in a low concentration range, sodium ions are eluted and affect the concentration detected. Generally, it is possible to temporarily reduce a concentration of sodium ions eluted by washing glass fibers with pure water, but the concentration of sodium ions eluted may increase again due to heating and aging in some cases. By coating a surface of the glass fiber with a resin not containing sodium ions, it becomes possible to restrain the elution of sodium ions from the glass fibers. In addition, it is also possible to use a resin by coating a surface of glass fibers with the resin not containing chloride ions or the like, which is a normal component homeostatically present in blood, in addition to sodium ions. FIG. 3 shows an SEM photograph of an example of a glass fiber not coated with a resin, and FIG. 4 shows an SEM photograph of an example of a glass fiber coated with a resin. Comparing FIGS. 3 and 4, it is understood that the resin is coated on a surface of each fiber composing the glass fiber.

Preferable examples of types of resin include acrylic resin, urethane resin, polyvinyl alcohol resin, epoxy resin, and the like, but are not particularly limited thereto. An adhesion amount of resin with respect to the glass fiber is not particularly limited as long as an amount thereof does not affect a separation function, but is preferably 1% to 10% by weight. A case in which an adhesion amount is 1% by mass or more is preferable because it is possible to sufficiently cover the surface of the glass fiber. In a case where an adhesion amount is 10% by mass or less, the resin is not accumulated between the glass fibers, and the resin coating can be performed without affecting the original blood cell separation function without lowering a void volume. The glass fibers coated with a resin are manufactured by immersing glass fibers in a resin solution or emulsion liquid, and then drying. This method is a simple and excellent manufacturing method, because the cost is low, a large amount of fibers can be manufactured, and the coating can be performed without using an expensive manufacturing apparatus required for film formation by vacuum vapor deposition.

An amount of a normal component which is derived from the member is required to be an amount with which the analysis of a concentration of a target component is performed at high accuracy, and by which the measurement of a dilution factor of a blood sample is not affected greatly. By suppressing an amount of sodium ions (an amount of sodium ions not derived from blood, that is, contamination components) in a diluent solution, which are derived from the members of the blood test kit, to about 0.03 times or less an amount of sodium ions in blood plasma, it is possible to maintain error accuracy at the time of calculation of a dilution factor at about 3%. For example, in a case where an amount of diluent solution is 360 μL, a volume of blood collected is 60 μL, and a proportion of blood plasma components is 55%, and in a case where an amount of sodium components which are derived from the members of the kit and may be contained in the diluent solution is 0.30 mmol/L or less with respect to the diluent solution, an amount of sodium components is about 2.3% by mass with respect to sodium ions derived from blood plasma. Therefore, test accuracies can be maintained within a range of error accuracy of about 2%. An amount of sodium components which are derived from the members of the kit and which may be contained in a diluent solution is preferably small, and is preferably 0.20 mmol/L or less, is more preferably 0.15 mmol/L or less, and even more preferably 0.10 mmol/L or less.

Figure 2:
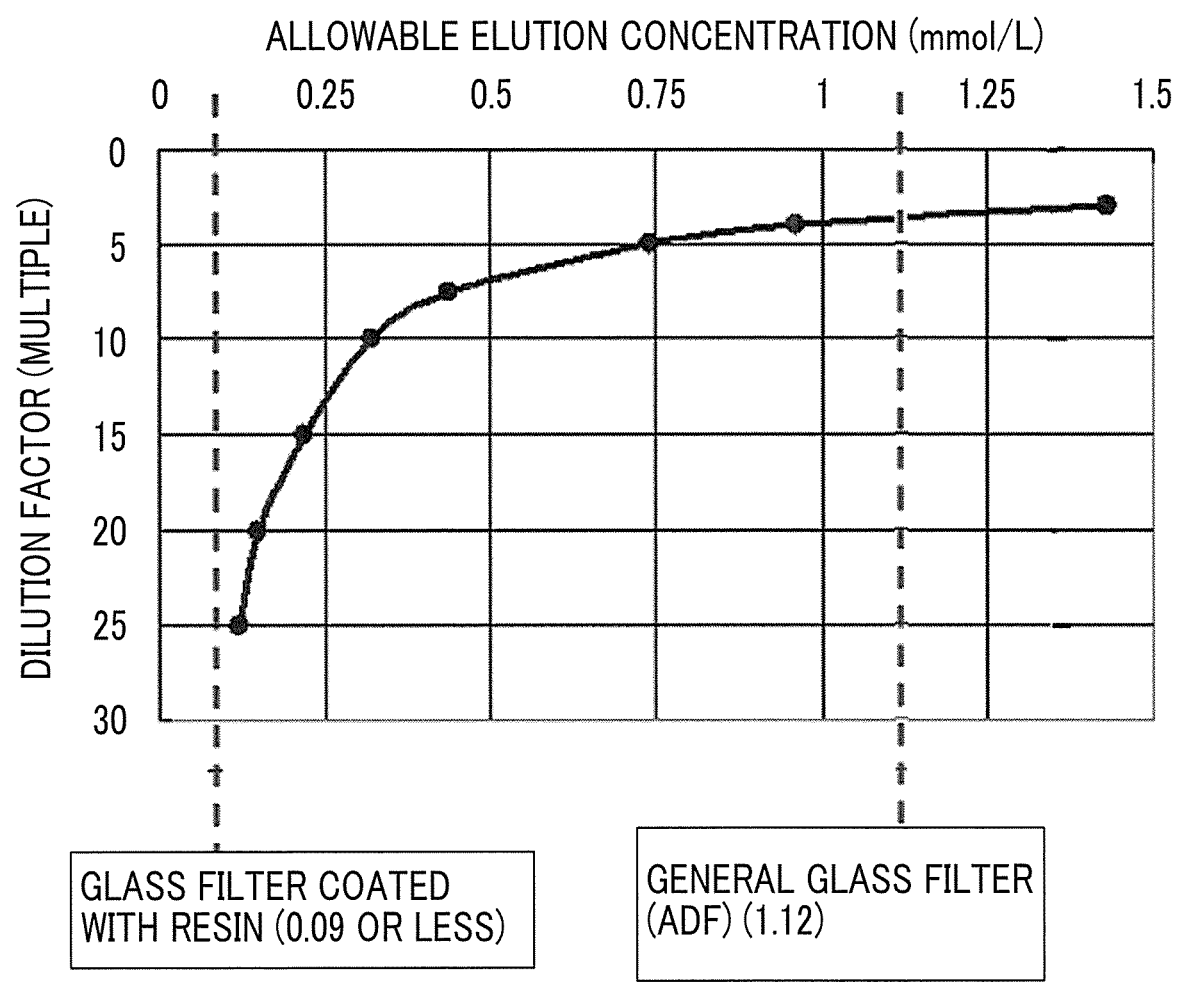
FIG. 2 shows results of calculation of an allowable elution concentration of sodium ions into a diluent solution (an allowable elution concentration eluted into the diluent solution).

As in the above-described calculation, in a case where an amount of normal components derived from the members is 0.02 times or less an amount of sodium ions in blood plasma, the calculation of a dilution factor can be maintained at an acceptable accuracy. For example, an allowable elution concentration of sodium ions in the diluent solution (an allowable elution concentration of sodium ions eluted into a diluent solution) is calculated with 360 μL of a diluent solution and a dilution factor within a range of 3 to 25 times. The results are shown in FIG. 2. In a case where a dilution factor of a diluent solution with respect to blood plasma components is 5, an allowable concentration of sodium ions in the diluent solution, which are derived from a member is about 0.70 mmol/L, that is, an allowable elution amount of sodium ions with respect to the diluent solution of 360 μL is about 5.8 μg. In addition, in a case of a dilution factor of 20, an allowable elution concentration of sodium ions in the diluent solution is about 0.16 mmol/L, that is, about 1.3 μg with respect to the diluent solution of 360 μL. Base on this, it is understood that as a dilution factor becomes larger, an allowable elution amount of sodium ions eluted into the diluent solution becomes rapidly high, and therefore the accuracy of a dilution factor decreases due to an elution amount in the diluent solution of a smaller volume as contamination.

In the blood test kit, a fiber lot is generally used for an aspirator for collecting blood, and a sodium salt of EDTA is used as an anticoagulant in this fiber lot. In addition, a glass fiber is used as an instrument for separating and recovering blood plasma, in which a small amount of sodium ions such as soda glass and sodium carbonate is contained. Soda glass is obtained by mixing and melting quartz sand ($SiO_2$), sodium carbonate ($Na_2CO_3$), and calcium carbonate ($CaCO_3$). In a case where a material of the gasket for holding the glass fiber and the sealing instrument for keeping the stored blood plasma in the second storing instrument is made of rubber, there is a case where a small amount of sodium ions is contained as a residue from NaOH cleaning for deproteinization, a release agent (mixture of sodium nitrate, sodium nitrite, and the like) which is used for molding, and the like. In a member which is a plastic (resin) molded product, a small amount of Na may be contained on the surface thereof in some cases. This is because, as metal elements in the release agent used for resin molding, sodium is contained together with tin, zinc, calcium, and the like.

As described above, glass fibers are used as separation membranes capable of separating blood cells. Glass fibers are coated with a resin to prevent the glass fibers from mixing into a diluent solution, as sodium ions derived from the kit. The inventors of the present invention checked an amount of elution from members other than glass fiber, and the amount is around about 10% of the whole. The amount thereof can be suppressed to a contamination amount of sodium ions of 2% or less with respect to an amount of sodium ions in blood plasma by preventing the elution of sodium ions from glass fiber. Therefore, it is understood that it becomes possible to analyze a target sample with high accuracies.

The blood test kit of the embodiment of the present invention includes a diluent solution for diluting the blood sample, a first storing instrument for storing the diluent solution, a separation instrument (composed of glass fibers coated with resin) for separating and recovering blood plasma from the blood sample diluted with the diluent solution, a holding instrument for holding the separation instrument, a second storing instrument for storing the recovered blood plasma, and a sealing instrument for keeping the stored blood plasma within the second storing instrument. As examples of the blood test kit of the embodiment of the present invention, the kit can include a diluent solution for diluting components in a blood sample, a first storing instrument in which the diluent solution is stored, a separation instrument for separating and recovering blood plasma from the blood sample diluted with the diluent solution, a holding instrument for holding glass fiber coated with resin and glass fiber coated with resin, a second storing instrument for storing the recovered blood plasma, a sealing instrument for keeping the stored blood plasma in the second storing instrument, a needle or a lancet for pricking the skin to allow blood to flow out of the skin, a strip of bandage or a disinfection member to be put on the wound (for example, nonwoven fabrics impregnated with isopropanol (70% isopropanol and the like), ethanol, or the like), an instruction manual, and the like.

Regarding the first storing instrument and the second storing instrument, one instrument may be used as both the first storing instrument and the second storing instrument, or an embodiment in which instruments are provided separately may be used. The first storing instrument and the second storing instrument are preferably made of a transparent material such that a patient or a measurer who performs measurement of a dilution factor and analysis of a target component to be analyzed can check a diluent solution in the storing instrument, by which the blood is diluted.

As the holding instrument for holding the separation instrument, an aspect of a gasket is preferable. In addition, as the sealing instrument, in a case where the storing instrument is an instrument having a tubular shape, and the like, it is possible to use a cap capable of being used as a lid for the opening, a lid having a helical groove, a rubber closure, and the like.

With the above configuration, by imparting the function of separating blood plasma from blood cells to the container in which the blood is mixed with the diluent solution immediately after diluting the blood with the diluent solution, it is possible to eliminate the influence on the stability of the blood components and the variation of the components due to hemolysis from blood cells, and to impart the stability to the specimen after blood collection.

The blood test kit of the embodiment of the present invention is capable of realizing a method in which a target component to be analyzed can be analyzed at high measurement accuracy even with a volume of blood collection of 100 µL or less, and is preferably a kit including an instruction manual in which information that measurement can be accurately performed even with a small volume of blood collection of 100 µL or less, and the like is described for a patient.

Specific Example of Blood Test Kit

In one of the preferred embodiments, as preferred specific instruments of the kit, it is possible to use an instrument which is disclosed in FIG. 1 to FIG. 13 of JP3597827B and uses glass fiber coated with resin as a separation instrument. FIG. 1 of JP3597827B is incorporated as FIG. 1 of the present application.

A blood separation instrument 1 includes a blood collection container 2 (storing instrument in which a diluent solution is stored, which may be referred to as the first storing instrument in some cases. This is a storing instrument for storing a dilution of a blood sample), a tubular body 3 capable of being to fit into the blood collection container 2 so as to be inserted (second storing instrument for storing recovered blood plasma), a cap piston 4 capable of being capped on the tubular body 3, and a sealing lid 5 (sealing instrument) provided at a lower end of the cap piston 4. Before use, an upper end opening portion of the blood collection container 2 is sealed by a cap 6 via a packing 7, as shown in FIG. 1. The storing instrument for storing a diluted blood sample of the present invention corresponds to a combination of the blood collection container 2 and the tubular body 3 in the configuration of FIG. 1. That is, the storing instrument for storing a diluted blood sample may be one or a combination of two or more thereof.

The blood collection container 2 is made of a transparent material and has a cylindrical shape. At the upper end portion thereof, a screw portion 8 is formed on the outer surface, and a locking portion 9 is protruded toward the inner surface. In addition, at a lower end portion of the blood collection container 2, a bottom portion 10 having an inverted conical shape is formed, and a cylindrical leg portion 11 is formed around the bottom portion 10. The leg portion 11 has the same outer diameter as a sample cup used at the time of an analytical test of blood, and at positions opposite to the lower end thereof, slit grooves 12 are preferably formed in a vertical direction, respectively. Furthermore, a predetermined volume, for example, 500 mm³ of a diluent solution 13 may be put in the blood collection container 2 in advance, as shown in FIG. 1.

The tubular body 3 is made of a transparent material and has a cylindrical shape, and at an upper end portion thereof, an expanded diameter section 14 is formed. The expanded diameter section 14 is connected to a main body portion 16 via a thin portion 15. A reduced diameter section 18 is formed at the lower end portion of the tubular body 3, and a protruded locking portion 19 is formed on the inner surface of the reduced diameter section 18. Furthermore, at a lower end portion of the reduced diameter section 18, an outer flange portion 20 (holding instrument) is formed, a lower end opening portion of the outer flange portion 20 is covered with a filtration membrane 21 (glass fiber coated with resin), and the filtration membrane 21 allows blood plasma in the blood to pass through and prevents passage of the blood cells.

A cover 22 made of silicone rubber is attached to the outer periphery of the reduced diameter section 18 (FIG. 1).

The cap piston 4 is constituted by a substantially cylindrical knob portion 26 and a mandrel portion 27 concentric with the knob portion 26 and extending downward. At an inner upper end portion of the knob portion 26, a cylindrical space 28 into which the expanded diameter section 14 of the tubular body 3 is capable of being fitted to be inserted is formed, and the knob portion is threaded in a lower portion into which a screw can screw. The mandrel portion 27 has a lower end portion 29 formed in a pin shape, and the sealing lid 5 is attachably and detachably provided on the lower end portion 29 (refer to FIG. 1). The sealing lid 5 is made of silicone rubber.

Specifically, the operation of separating and recovering blood plasma from a dilution of a blood sample is performed as below. The collected blood is added to the blood collection container 2 storing the diluent solution, and then the blood and the diluent solution are thoroughly shaken to be mixed while noting that bubbles are not generated by holding an upper portion of the blood collection container 2. Next, the tubular body 3 holding a glass fiber 21 coated with resin (for preventing solution leakage due to infiltration into a side surface of a cylinder at the time of separating blood plasma from blood cells) is inserted into the blood collection container 2 such that the glass fiber coated with resin faces downward, and the filtration membrane is slowly pushed into the bottom of the blood collection container 2 at a constant speed. At this time, the blood plasma passes through the glass fiber coated with a resin of the tubular body 3 and then floats on the upper portion, and the blood cells remain on the lower portion of the blood collection container 2. Thereafter, the cap piston 4 is slowly pushed into the tubular body 3, by which mixing of the blood plasma with the blood cells due to backflow is prevented by the sealing lid 5.

A method for separating blood by the instruments described above is described in detail in paragraphs 0023 to 0026 and FIG. 12 and FIG. 13 of JP3597827B, the contents of which are incorporated in the present specification.

The number of various components contained in the blood test kit of the present invention is not particularly limited, and each component may be one, or there may be a plurality of, for example, 2 or more thereof.

The material of the member included in the blood test kit of the present invention is preferably a synthetic resin from the viewpoints of difficulty in breakage, sanitation, price, and the like. Examples thereof include polyethylene, polypropylene, polyvinyl chloride, polyvinylidene chloride, polystyrene, polyvinyl acetate, polyurethane, polyethylene terephthalate, polylactic acid, acrylonitrile butadiene styrene resin (ABS resin), acrylonitrile styrene resin (AS resin), acrylic resin (PMMA), polycarbonate, silicone resin, and the like.

The blood test kit of the present invention can provide all members in an aspect in which the members are stored in the storing container.

[2] Others

The present invention provides a blood analysis method using the blood test kit configured as described in [1] of the present specification. The blood analysis method includes an aspect which is a medical practice (practice performed by a doctor) for humans and an aspect which is not a medical practice for humans (for example, an aspect in which a person who performs blood collection is a patient himself and an analyzer is a person other than a doctor, an aspect for non-human animals, and the like). The blood analysis method of the present invention may be performed by the self-blood collection in which a subject to be tested collects blood by himself, or may be performed by the general blood collection in which a qualified person such as a doctor collects blood using a syringe. As a preferred embodiment, a patient pricks the fingertip and the like by himself using an instrument equipped with a small blade such as a lancet, and then collects blood flowing out of the skin.

A biological specimen which is a target to be analyzed using the blood test kit of the embodiment of the present invention is blood, and the blood is a concept of including serum or blood plasma. The origin of blood is not limited to humans, and may be mammals, birds, fish, and the like which are animals other than humans (non-human animals). Examples of the animals other than humans include horses, cows, pigs, sheep, goats, dogs, cats, mice, bears, pandas, and the like. The origin of a biological specimen is preferably humans.

In a case of performing the analysis using the blood test kit of the embodiment of the present invention, the target component to be analyzed is not limited and any substance contained in blood is a target. Examples thereof include biochemical test items in blood used for clinical diagnosis, markers of various diseases such as tumor markers and hepatitis markers, and the like, and include proteins, saccharides, lipids, low molecular weight compounds, and the like. In addition, not only a concentration of a substance is measured, but also an activity of a substance having an activity such as an enzyme is targeted. Analysis of each target component can be carried out by a known method.

EXAMPLES

Hereinafter, examples, comparative examples, and reference examples of the present invention will be explained.

Reference Example 1

1. Composition of Diluent Solution

A diluent solution was prepared with the following composition. As osmotic pressure, a value measured by using OSMOATAT OM-6040 (manufactured by ARKRAY, Inc.) is shown. A unit of the osmotic pressure is an osmotic pressure that 1 kg of water of a solution has, and indicates millimoles of ions.

| | |
|---|---|
| HEPES | 50 mmol/L |
| 2-amino-2-methyl-1-propanol (AMP) | 50 mmol/L |

-continued

| | |
|---|---|
| D-Mannitol | 284 mmol/L |
| Lithium chloride | 1 mmol/L |
| EDTA-2K | 0.8 mmol/L |
| Pyridoxal phosphate (PALP) | 0.05 mmol/L |
| Thiabendazole | 0.0001% by mass |
| Amikacin sulfate | 0.0003% by mass |
| Kanamycin sulfate | 0.0005% by mass |
| Meropenem trihydrate | 0.0005% by mass |
| Osmotic pressure | 355 mOsm/kg |
| pH 7.4 | |

2. Measurement of Concentration of Sodium

The measurement of a concentration of sodium in the diluent solution prepared in 1. was carried out by the enzyme activity method utilizing that β-galactosidase is activated by sodium, which is that each concentration of sodium in the diluent solution and β-galactosidase activity are in a proportional relationship. Specifically, after diluting the diluent solution of the blood five times by using purified water not containing sodium ions, 3 μL was weighed, 52 μL of a first reagent prepared as described below was added thereto, and then heated at 37° C. for 5 minutes. 26 μL of a second reagent prepared as described below was added thereto, and the change in absorbance was obtained by measuring an absorbance during 1 minute at a main wavelength of 410 nm and a complementary wavelength of 658 nm by using JCA-BM6050-type automatic biochemistry analyzer (manufactured by JEOL Ltd.). The concentration of sodium was measured from a calibration curve prepared in advance.

(Preparation of Reagent for Measuring Sodium)

A reagent for measuring sodium having the following composition was prepared.

| | |
|---|---|
| First reagent | |
| HEPES/LiOH (pH 8.0) | 100 mmol/L |
| D-Mannitol | 60 mmol/L |
| N-acetylcysteine | 30 mmol/L |
| Magnesium sulfate | 1.52 mmol/L |
| β-galactosidase | 1.1 kU/L |
| TRITON X-100 | 0.05% by mass |
| Second reagent | |
| HEPES/LiOH (pH 8.0) | 100 mmol/L |
| o-Nitrophenyl-β-D-galactopyranoside | 15 mmol/L |

A concentration of sodium ions eluted from the glass fibers was obtained by the following procedure.

A glass fiber with a thickness of 0.5 to 0.8 mm was punched out into a circular shape having a diameter of 6.3 mm using a blade, and four sheets were stacked and stored in a holder which is a holding instrument to constitute a separation instrument. The holder in which the glass fiber was stored was immersed in and thoroughly mixed with 360 μL of a diluent solution that was prepared as described above and stored in the storing container, and then a supernatant liquid of the diluent solution was taken out with a pipette to measure a concentration of sodium ions 10 times using the reagent for measuring sodium described above. Meanwhile, a concentration of sodium ions eluted from a blood suction member containing an anticoagulant and other members is obtained by subtracting an extent of contribution of the holder in which the glass fiber was stored, from a total concentration of sodium ions (measured 10 times) of a diluent solution obtained by subjecting all separation instruments to filtration operation.

A coefficient of variation (CV) (%), which is a measure of an average value and variation in amount of Na ions eluted into a diluent solution, was obtained for glass fibers coated with resin (GF/DVA: product name (manufactured by GE Healthcare), VF2: product name (manufactured by GE Healthcare)) and general glass fibers (ADF: product name (manufactured by Nippon Paul)); a blood suction member containing an anticoagulant; and other members. The results are shown in Table 1. The resin in GF/DVA: product name (manufactured by GE health care company) is polyvinyl alcohol, and the resin in VF2: product name (manufactured by GE health care company) is polyvinyl alcohol. In addition, in GF/DVA: product name (manufactured by GE Healthcare), and VF2: product name (manufactured by GE Healthcare), a coating amount of resin is 6% by mass with respect to a mass of glass fibers.

TABLE 1

| Type of filtration membrane for blood plasma | Volume of diluent solution (μL) | Concentration n of Na ions eluted into diluent solution = 3 average value (mmol/L) | CV of concentration of Na ions eluted into diluent solution (%) | Note |
|---|---|---|---|---|
| GF/DVA (manufactured by GE health care company) | 360 | 0.09 | 2.2 | Reference Example |
| VF2 (manufactured by GE health care company) | 360 | 0.09 | 2.2 | Reference Example |
| ADF (manufactured by Nippon Paul) | 360 | 1.12 | 3.8 | Comparative example |
| Blood suction member containing anticoagulant, and other members | 360 | 0.23 | 2.8 | Comparative example |

In FIG. 2, a concentration level of sodium ions eluted into a diluent solution with respect to the diluent solution is illustrated by a dotted line in a case of using general glass fibers (ADF) and in a case of using glass fibers coated with resin (GF/DVA, VF2).

Based on the results of FIG. 2 and Table 1, it was found that by coating the glass fiber which is the member of the blood test kit with resin in a case where sodium ions which are components homeostatically present blood are used as a standard substance, it is possible to lower a concentration of sodium eluted into the diluent solution with respect to the diluent solution to 0.09 mmol/L in an average value and to lower CV, and that an allowable elution concentration of sodium ions in the diluent solution, which is for calculating a dilution factor at high accuracies is sufficiently clear in a wide range of a large dilution factor.

Reference Example 2

1. Preparation of diluent solution with which small volume of blood sample is diluted After informed consent was obtained from a volunteer patient, about 30 mL of blood collected from the vein by a syringe was obtained in a blood collection tube. Blood plasma was obtained in advance with a centrifuge from half of this blood collected. From this collected blood, 90 μL and 19 μL were precisely weighed 10 times respectively with a micropipette, and each was mixed into 360 μL of the same diluent solution as the diluent solution prepared in Reference Example 1. The diluent solution mixed with blood plasma was filtered using the holder in which glass fibers (GF/DVA, ADF) used in Reference Example 1 were stored. Using this diluted blood plasma after filtration as a specimen, a concentration of sodium ions was measured in the same manner as in Reference Example 1, and a calculated value of a dilution factor and CV (%) which is an index of variation in measured dilution factors were obtained. The results are shown in Table 2.

TABLE 2

| Amount of blood plasma (μL) | Volume of diluent solution (μL) | Dilution factor (calculation value) | Dilution factor (measurement value) | CV of measured dilution factor (%) | Glass filter | Note |
|---|---|---|---|---|---|---|
| 90 | 360 | 5 | 4.7 | 4.3 | ADF | Comparative Level 1 |
| 90 | 360 | 5 | 5 | 2.8 | GF/DVA | Reference Level 1 |
| 19 | 360 | 19.9 | 15.4 | 4.7 | ADF | Comparative Level 2 |
| 19 | 360 | 19.9 | 19.7 | 3.4 | GF/DVA | Reference Level 2 |

From Table 2, it is understood that, in a case of using the glass fiber coated with resin, in a stage of obtaining a mixed solution of blood plasma by filtering a mixed solution of blood and a diluent solution, an amount of sodium components mixed was extremely small, a dilution factor when blood plasma was diluted, which is approximately the same as an actual dilution factor value, is obtained, and it is possible to suppress variation between measurements to be low.

Example 1

1. Measurement of Alanine Transaminase (ALT) and Aspartate Aminotransferase (AST)

Immediately after collecting the blood from the vein using a syringe in Reference Example 2, a lancet was used for pricking the fingertip of the same patient of the blood collection to allow blood to flow out of the skin of the fingertip, and then the patient collects liquid of about 30 μL to 40 μL. The blood was mixed into 360 μL of the same diluent solution as the diluent solution prepared in Reference Example 1. A mixed solution of blood and the diluent solution was filtered with the glass fiber coated with resin (GF/DVA) used in Reference Examples 1 and 2 to be separated into a blood cell component. Therefore, a diluent solution of the blood plasma component of the blood sample was obtained. Thereafter, the diluent solution was sealed and transported to another facility capable of the test. After the transportation, the diluent solution was taken out, and when a dilution factor was measured in the same manner as in the measuring method of a dilution factor using sodium ions of the blood in Reference Example 2, a dilution factor was 18.7. Based on this, it was found that a volume of blood collection was slightly less than 40 μL. When concentrations of ALT and AST in this diluted sample was measured using a commercially available measurement kit (Transaminase CII-Test Wako: manufactured by Wako Pure Chemical Industries, Ltd.), with respect to results in which an ALT value and an AST value, which were measured using a diluent solution of blood plasma which was obtained by centrifugation, was not underwent filtration in Reference Example 1, and was prepared in Reference Example 2, were 18 U/L and 37 U/L, respectively, results almost corresponding to the above results were obtained, in which an ALT value and an AST value, which were analyzed from the diluent solution obtained by diluting the blood collected from the fingertip as described above, were 18 U/L and 35 U/L, respectively. Therefore, the effect of the present invention was confirmed.

EXPLANATION OF REFERENCES

1: blood separation instrument
2: blood collection container
3: tubular body
4: cap piston
5: sealing lid
6: cap
7: packing
8: screw portion
9: locking portion
10: bottom portion
11: leg portion
12: slit groove
13: diluent solution
14: expanded diameter section
15: thin portion
16: main body portion
18: reduced diameter section
19: protruded locking portion
20: outer flange portion
21: filtration membrane
22: cover
26: knob portion
27: mandrel portion
28: space
29: lower end portion
31: level difference portion
33: upper end portion
34: top portion

What is claimed is:

1. A blood test kit for analyzing a concentration of a target component in a blood sample using a normal component which is homeostatically present in blood, the kit comprising:
    a diluent solution for diluting the blood sample;
    a first storing instrument for storing the diluent solution;
    a separation instrument for separating and recovering blood plasma from the blood sample diluted with the diluent solution;
    a holding instrument for holding the separation instrument;
    a second storing instrument for storing the recovered blood plasma; and
    a sealing instrument for keeping the stored blood plasma within the second storing instrument,
    wherein the separation instrument is composed of glass fibers coated with a resin,
    the resin is selected from the group consisting of urethane resins, polyvinyl alcohol resins, and epoxy resins,
    a coating amount of the resin is 1% to 10% by mass with respect to a mass of the glass fibers, and
    the resin does not accumulate between the glass fibers so that the glass fibers are coated without lowering a void volume.

2. The blood test kit according to claim 1, wherein a volume of the diluent solution is four or more times a volume of the blood plasma.

3. The blood test kit according to claim 1, wherein the normal component which is homeostatically present in blood is sodium ions or chloride ions.

4. The blood test kit according to claim 1, wherein the normal component which is homeostatically present in blood is sodium ions or chloride ions, and another normal component which is homeostatically present in blood.

5. The blood test kit according to claim 4, wherein the other normal component is total protein or albumins.

6. A blood analysis method, comprising:
    a step of diluting a collected blood sample with a diluent solution using the blood test kit according to claim 1;
    a step of determining a dilution factor by using a normal value of a normal component which is homeostatically present in blood; and
    a step of analyzing a concentration of a target component in the blood sample.

* * * * *